United States Patent
Fuchshuber et al.

(10) Patent No.: US 7,118,734 B1
(45) Date of Patent: Oct. 10, 2006

(54) NON-AQUEOUS LIQUID SHAMPOO COMPOSITION

(75) Inventors: Lilian Fuchshuber, Victoria (AU); Ron Harding, Victoria (AU)

(73) Assignee: Connetics Australia Pty Ltd., Victoria (AU)

(*) Notice: Subject to any disclaimer, the term of this patent is extended or adjusted under 35 U.S.C. 154(b) by 0 days.

(21) Appl. No.: 10/069,448

(22) PCT Filed: May 1, 2000

(86) PCT No.: PCT/AU00/00389

§ 371 (c)(1), (2), (4) Date: Aug. 7, 2002

(87) PCT Pub. No.: WO00/66172

PCT Pub. Date: Nov. 9, 2000

(30) Foreign Application Priority Data

Apr. 29, 1999 (AU) .................................. PQ0029

(51) Int. Cl.
*A61Q 5/02* (2006.01)

(52) U.S. Cl. ............ 424/70.11; 424/70.1; 424/70.22; 424/70.24; 514/881

(58) Field of Classification Search .......... 424/70.1, 424/70.11, 70.24, 70.22
See application file for complete search history.

(56) References Cited

U.S. PATENT DOCUMENTS

| | | | |
|---|---|---|---|
| 3,152,046 A | 10/1964 | Ales | |
| 4,126,674 A | 11/1978 | Mausner | |
| 4,253,993 A * | 3/1981 | Ramsey et al. | 510/120 |
| 5,104,645 A * | 4/1992 | Cardin et al. | 514/345 |
| 5,559,092 A | 9/1996 | Gibson et al. | |
| 5,643,601 A | 7/1997 | Gross et al. | |
| 5,866,152 A | 2/1999 | Takebayashi et al. | |
| 5,993,787 A | 11/1999 | Sun et al. | |
| 6,207,694 B1 * | 3/2001 | Murad | 514/396 |

FOREIGN PATENT DOCUMENTS

| | | |
|---|---|---|
| AU | A-50181/90 | 2/1990 |
| DE | 38 16 447 A | 11/1988 |
| EP | 0028525 | 10/1980 |
| EP | 0 596 135 A | 5/1994 |
| EP | 0 872 230 A | 10/1998 |
| EP | 0 988 852 A | 3/2000 |
| EP | 1 048 288 A | 11/2000 |
| FR | 1 098 828 A | 8/1955 |
| FR | 2 225 145 A | 11/1974 |
| FR | 2 252 403 A | 6/1975 |
| GB | 2 274 060 A | 7/1994 |
| WO | WO 87/04617 | 8/1987 |
| WO | WO 87/04617 A | 8/1987 |
| WO | WO 98/10742 | 3/1998 |

OTHER PUBLICATIONS

Remington: The Science and Practice of Pharmacy, Mack Publishing Co., 19th Edition, 1995, pp. 1395-1406.

* cited by examiner

*Primary Examiner*—Jyothsna Venkat
(74) *Attorney, Agent, or Firm*—Townsend and Townsend and Crew LLP

(57) ABSTRACT

This invention relates to compositions suited to use as hair shampoos, and particularly those developed with a view to the treatment of a hair borne infestation, or of a skin disease of the scalp in addition to the primary purpose of hair cleaning and conditioning. In a first aspect of the invention there is provided a substantially non-aqueous liquid shampoo composition comprising at least one detergent, at least one active agent incompatible with water, an organic bulking agent and shampoo excipients, said organic bulking agent being miscible with water and miscible with said at least one detergent and shampoo excipients. It has been surprisingly found that replacing an aqueous bulking agent such as water with an organic compound which is compatible with active agents insoluble in water but which itself is miscible with water and miscible with detergents can produce a cosmetically and aesthetically acceptable non-aqueous liquid shampoo, particularly one having acceptable foaming characteristics.

12 Claims, No Drawings

NON-AQUEOUS LIQUID SHAMPOO COMPOSITION

This invention relates to compositions suited to use as hair shampoos, and particularly those developed with a view to the treatment of a hair borne infestation, or of a skin disease of the scalp in addition to the primary purpose of hair cleaning and conditioning.

BACKGROUND

Hair shampoos are a common household commodity in many communities around the world. The properties of a good shampoo often depend upon the intended application, but may include the ability to cleanse the hair and scalp of the user thoroughly, but without stinging, irritation or the removal of excess natural oils from the scalp, cosmetic and aesthetic characteristics including the imparting of lustre, softness and manageability and the formation of foam necessary for removal of dirt particles. Consumers consider foaming ability an important aesthetic consideration in assessing the acceptability of a shampoo.

Shampoos may be variously formulated as liquids, creams, pastes, aerosols or dry formulations. The majority are liquids, either clear or pearlised. The principal constituents of most liquid shampoos can be classified as detergents, thickeners, foam stabilisers and boosters, perfumes, preservatives, diluents or bulking agents (usually water), conditioning agents or emollients, pearlisers/opacifiers and colours. The bulking agents are included primarily for commercial purposes, so as to allow a consumer to dispense a typical amount of shampoo so as to achieve a desirable level of lather and cleaning.

In addition, some shampoos having a specialised application, such as minimisation of eye sting, treatment of dandruff or other scalp conditions, or which are formulated for specific hair types such as dry, oily, coloured or permed hair often contain further additives to fulfil their advertised purpose. It is desirable to combine the cleansing characteristics of a shampoo with medicated treatments for hair borne or skin-based diseases at least for convenience, if not for ease of application.

Shampoos in liquid form usually contain a large proportion of water. Water is frequently used as the bulking agent in liquid shampoos, because of its inert properties, its miscibility with other shampoo constituents, its low cost, and its ease of removal from hair during the normal washing process.

However, in instances where it is desirable to include an additive in a liquid shampoo, and in which the additive is not compatible with water, such as some medicaments, there is a need to find an alternative to the use of water as a bulking agent.

There are many difficulties in formulating a non-aqueous shampoo. For example, the use of alcohols in shampoos may reduce or destroy desirable foam formation. Alternatively, oils are often too greasy and so are cosmetically unacceptable in the amounts required. Exotic non-aqueous bulking agents are commercially prohibitive because of their high cost.

Various medicated compositions exist which are directed to the treatment of scalp or skin diseases, or to lice infestation in hair for example. U.S. Pat. No. 5,993,787 (JOHNSON & JOHNSON CONSUMER PRODUCTS INC) is directed to a topical preparation for treatment of fungal infections. This formulation is presented in the form of a lotion and has no cleansing characteristics such as are desirable in a medicated shampoo. Similarly, EP0028525 (ORION-YHTYMA OY) is directed to a topical solution applied to the scalp for treatment of alopecia, and AU599086 is directed to a topical treatment of scalp diseases but not in a shampoo format.

Other patented formulations are aqueous and so are not well suited to the incorporation of active agents which are insoluble in water. Amongst this class of prior art disclosures are U.S. Pat. No. 5,866,152 (SUMITOMO CHEMICAL COMPANY) directed to shampoos for treatment of lice, and U.S. Pat. No. 5,559,092 (CHEESEBOROUGH-PONDS USA CO.DIVISION OF CONOPCO, INC).

It is an object of the present invention to produce a non-aqueous liquid shampoo which contains an active agent such as for treatment of scalp or skin diseases, or for treatment of hair infestations in a composition which imparts desirable aesthetic characteristics to the hair being treated, has a satisfactory cleansing and foaming capacity, and which does not have undesirable effects on the user.

SUMMARY OF THE INVENTION

Therefore, in a first aspect of the invention there is provided a substantially non-aqueous liquid shampoo composition comprising at least one detergent, at least one active agent incompatible with water, an organic bulking agent and shampoo excipients, said organic bulking agent being miscible with water and miscible with said at least one detergent.

It has been surprisingly found that replacing an aqueous bulking agent such as water with an organic compound which is compatible with active agents insoluble in water but which itself is miscible with water and miscible with detergents can produce a cosmetically and aesthetically acceptable non-aqueous liquid shampoo, particularly one having acceptable foaming characteristics.

Throughout this specification, the reference to a "non-aqueous" shampoo is not intended to exclude compositions that contain a minimum amount of water by virtue of their incorporation of constituents commonly used in shampoos such as surfactants which may contain a proportion of water. Therefore, reference to a non-aqueous shampoo composition is intended to include compositions where no water per se is added to the composition. In the context of the invention therefore, compositions containing no greater than 20%, more preferably no greater than 15% of water based on the total weight of the composition, the water present in the composition by virtue of its inclusion in normal shampoo constituents may be defined as "non-aqueous".

The use of the term "comprising" throughout this specification is intended to mean that constituents other than those specifically identified may be incorporated within the compositions of the invention, and is not intended to exclude specific constituents or components not specifically identified as being present in the shampoo compositions of the invention.

In a preferred embodiment of the invention, the non-aqueous liquid shampoo composition may additionally include one or more of a solvent, a foam booster and/or a mild surfactant.

In a further preferred embodiment, the organic bulking agent is present in an amount of at least 20%, more preferably 50% based on the total weight of the composition. Desirably, the organic bulking agent is present in amounts no less than 10%

Organic compounds, which do not inhibit foam formation, are preferred as bulking agents.

The organic bulking agent may be selected from polyethylene glycol (PEG), monohydric alcohols (examples are alcohols with $C_2$ to $C_6$ chain), polyhydric alcohols (examples are propylene glycol, hexylene glycol and glycerol), glycol ethers (examples are pluronic surfactants), ketones (examples are cyclohexanone and diacetone alcohol) and short chained esters (examples are acetates, lactates and carbonates)

Preferably, the organic compound is PEG with a molecular weight of 200–800.

In a more preferred embodiment, the organic bulking agent is PEG 400.

In an alternative preferred embodiment, the organic bulking agent is propylene glycol.

Detergents which are suited to incorporation in the compositions of the invention may include commonly used shampoo detergents which are usually anionic and inexpensive. Sodium laureth sulphate is one possible choice and is easily the most widely used in current shampoos (particularly in Europe). Alternative detergents include alkyl sulphates, alkyl ether sulphates, α-Olefin sulphonates, paraffin sulphonates, isethionates, sarcosinates, taurides, acyl lactylates, sulphosuccinates, carboxylates, protein condensates, betaines, glycinates, amine oxides and alkyl polyglycosides. Other alternatives will be apparent to a skilled addressee.

Preferred detergents according to the invention may be selected from alkyl sulphates (examples are sodium lauryl sulphate and ammonium lauryl sulphate), alkyl ether sulphates (examples are sodium laureth sulphate and ammonium laureth sulphate) and sulphsuccinates (example is dialkyl sodium sulfosuccinate).

In a more preferred embodiment, the detergent is a synthetic detergent and is selected from the group consisting of alkyl sulphates and alkyl ether sulphates.

Foam boosters according to a preferred embodiment of the invention may be selected from alkyl (amido) betaines (an example is cocamidopropyl betaine), alkanolamides (examples are cocamide DEA and lauramide DEA) and amine oxides (examples are cocamine oxide and lauramine oxide).

A mild surfactant suited to use in preferred compositions of the invention may be any which are commonly used in liquid shampoos. The term "mild" will be understood by those skilled in the art.

The shampoo of the invention includes an active agent which would not be compatible in an aqueous shampoo. Compatibility includes such factors as solubility and stability. The active agent may be a compound which needs to be solubilised in the composition to be effective and/or cosmetically acceptable. The active agent may be a pharmaceutical ingredient.

Examples of suitable pharmaceutical ingredients include antifungals and antidandruffs such as ketoconazole, antipsoriatics such as betamethasone valerate, antipruritics such as menthol, hair loss preventative agents such as minoxidil, non-steroidal anti-inflammatories, such as piroxicam, ketoprofen or ibuprofen and antibacterials.

Preferably, the pharmaceutical ingredient is an antifungal agent, more preferably clotrimazole or ketoconazole.

The clotrimazole pharmaceutical ingredient may be present in the shampoo composition in an amount of 0.05% to 10.00% based on the total weight of the composition.

In a preferred embodiment, the clotrimazole is present in an amount of about 2% based on the total weight of the composition.

Although the organic bulking agent may solubilise the active agent, a solvent in addition to the organic compound bulking agent may be required to achieve solubilisation of the active agent. Examples of solvents that may be used are alkyl pyrolidones (examples are caprylyl pyrrolidone and lauryl pyrrolidone), ketones (examples are cyclohexanone and diacetone alcohol), amines (examples are pyrrole and N-methyl-2-pyrrolidone), esters (examples are acetates, lactates and carbonates), aldehydes, aromatics (and example is alkyl benzene) monohydric alcohols (examples are alcohols with $C_2$ to $C_6$ chain) and polyhydric alcohols (examples are propylene glycol, hexylene glycol and glycerol).

The solvent required will depend on the solubility profile of the active agent to be incorporated.

The non-aqueous shampoo of the invention may include other excipients, including thickening agents such as hydroxypropyl cellulose, carbomers and hectorite clays, as well as a number of additives commonly included in shampoos such as vitamins, essential oils, fruit extracts, dyes or perfumes.

The pH of the liquid shampoo composition may be adjusted so as to provide a stable composition.

The pH of the final composition may be in the range of 4–10, for a clotrimazole liquid shampoo preferably in the basic range of 7–9.

In a most preferred embodiment of the invention, the non aqueous shampoo includes active agent in an amount of 0.05–8% w/w, solvent in an amount of 5–15% w/w, organic bulking agent in an amount of 2–5% w/w, surfactant/booster in an amount of 1–5% w/w, and detergent in an amount of 5–25%.

One particular embodiment of the invention desirable for commercial purposes is that according to example 1 below.

In an alternate embodiment of the invention, there is provided a method of topically treating a dermal infection or condition including applying the non-aqueous shampoo according to the invention to the skin or hair of a patient in need of such treatment which composition preferably contains an antifungal agent. In a preferred embodiment, the antifungal agent is clotrimazole.

In a further embodiment of the invention there is provided the use of an organic bulking agent for the preparation of a non-aqueous shampoo which comprises at least one detergent, an active agent incompatible with water, conventional carriers and shampoo excipients, said organic bulking agent being soluble in water and miscible with said at least one detergent. In this embodiment the organic bulking agent is desirably present in amounts greater than 10%, preferably greater than 20%, and more preferably greater than 60% by weight of the shampoo composition.

PREFERRED EMBODIMENTS OF THE INVENTION

The shampoo composition of the invention is illustrated by the following examples:

| Ingredient | Class | % W/W |
| --- | --- | --- |
| Clotrimazole | Pharmaceutical active | 2 |
| Surfadone LP 100 | Solvent | 10 |
| PEG 400 | Organic bulking agent | 60.5 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

Example 2

| Ingredient | Class | % W/W |
|---|---|---|
| Ketoconazole | Pharmaceutical active | 1 |
| Caprylyl pyrrolidone | Solvent | 10 |
| PEG 400 | Organic bulking agent | 61.5 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

Example 3

| Ingredient | Class | % W/W |
|---|---|---|
| Menthol | Pharmaceutical active | 5 |
| Caprylyl pyrrolidone | Solvent | 10 |
| PEG 400 | Organic bulking agent | 60.5 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |

Example 4

| Ingredient | Class | % W/W |
|---|---|---|
| Menthol | Pharmaceutical active | 5 |
| Ethanol | Solvent | 5 |
| Caprylyl pyrrolidone | Solvent | 10 |
| PEG 400 | Organic bulking agent | 56 |
| Hydroxypropycellulose | Thickening agent | 4 |
| Cocamidopropyl Betaine | Surfactant/booster | 2.5 |
| Sodium Cocoamphacetate | Mild surfactant | 5 |
| Sodium Lauryl Ether Sulfate | Detergent | 12 |
| Ammonium Lauryl Sulfate | Detergent | 10 |

Example 5

| Ingredient | Class | % W/W |
|---|---|---|
| Minoxidil | Pharmaceutical active | 2 |
| Caprylyl pyrrolidone | Solvent | 10 |
| Propylene glycol | Bulking agent | 60.5 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

Example 6

| Ingredient | Class | % W/W |
|---|---|---|
| Piroxicam | Pharmaceutical active | 1 |
| Caprylyl pyrrolidone | Solvent | 10 |
| PEG 400 | Organic bulking agent | 61.5 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

Example 7

| Ingredient | Class | % W/W |
|---|---|---|
| Ketoprofen | Pharmaceutical active | 2.5 |
| Caprylyl pyrrolidone | Solvent | 10 |
| PEG 400 | Organic bulking agent | 60 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

Example 8

| Ingredient | Class | % W/W |
|---|---|---|
| Ibuprofen | Pharmaceutical active | 2.5 |
| Caprylyl pyrrolidone | Solvent | 10 |
| PEG 400 | Organic bulking agent | 60 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

Example 9

| Ingredient | Class | % W/W |
|---|---|---|
| Betamethasone Valerate | Pharmaceutical active | 0.12 |
| Caprylyl pyrrolidone | Solvent | 10 |
| PEG 400 | Organic bulking agent | 62.38 |
| Hydroxypropycellulose | Thickening agent | 4 |
| Cocamidopropyl Betaine | Surfactant/booster | 2.5 |
| Sodium Cocoamphacetate | Mild surfactant | 4 |
| Sodium Lauryl Ether Sulfate | Detergent | 7 |
| Ammonium Lauryl Sulfate | Detergent | 10 |

The above examples were made using the following process:
The pharmaceutical active, solvent and organic bulking agent were combined together and stirred until a clear solution formed. In some instances the solution was gently warmed to 80° C. to assist with the dissolution of the pharmaceutical active.

With stirring the surfactant/booster, mild surfactant and detergent were added and stirred until a uniform mixture resulted. Each ingredient was intimately mixed into the solution prior to the addition of the next ingredient.

Where insoluble particulates remained these were filtered out. (Some surfactants are not totally soluble in a non-aqueous system. In those cases it was necessary to filter the composition prior to the addition of the thickening agent. The removal of the small quantity of insoluble material did not affect the performance of the shampoo.)

The solution was brought to a temperature of 50° C. and the thickening agent was added with constant stirring until the thickening agent had completely swelled out.

It will be appreciated that the invention is in no way limited to the above examples.

The following formulations were tested to determine the amount of water that compositions of the present invention would tolerate before unacceptable precipitation occurred.

Formulations:

| | % w/w | | | | | |
|---|---|---|---|---|---|---|
| Ingredients | 1 | 2 | 3 | 4 | 5 | 6 |
| Clotrimazole | 2.00 | 2.00 | 2.00 | 2.00 | 2.00 | 2.00 |
| Caprylyl pyrrolidone | 10.00 | 10.00 | 10.00 | 10.00 | 10.00 | 10.00 |
| PEG 400 | 60.50 | 55.50 | 50.50 | 45.50 | 40.40 | 35.50 |
| Cocoamidopropyl Betaine | 2.50 | 2.50 | 2.50 | 2.50 | 2.50 | 2.50 |
| Sodium Cocoamphacetate | 4.00 | 4.00 | 4.00 | 4.00 | 4.00 | 4.00 |
| Sodium Lauryl Ether Sulfate | 7.00 | 7.00 | 7.00 | 7.00 | 7.00 | 7.00 |
| Ammonium Lauryl Sulfate | 10.00 | 10.00 | 10.00 | 10.00 | 10.00 | 10.00 |
| Purified water | 4.00 | 9.00 | 14.00 | 19.00 | 24.00 | 29.00 |
| Total water content in formulation | 15.00 | 20.00 | 25.00 | 30.00 | 35.00 | 40.00 |

The thickening agent was not included as it had no other effect but to thicken the shampoo.

At the time of manufacture there were no visible indications that clotrimazole came out of solution. Samples of each formulation were stored at 4° C., room temperature and 50° C.

It was observed that after 3 days storage examples 5 and 6 showed clotrimazole crystal growth at 4° C. and at room temperature. After 1 week it was observed that examples 3 and 4 had crystal growth at 4° C. and room temperature but all the 50° C. samples remained clear. This indicated that temperature affected the active solubility. After several months, only 1 example that contained 15% w/w water, as crystal free at both 4° C. and room temperature. Example 2 at 4° C. and room temperature had some crystal growth.

The results suggested that for formulations containing clotrimazole it was preferable to keep the water content below 15% where the formulation would be stored at room temperature or less.

Foaming Performance

The following example was developed to compare the foaming characteristics of the shampoo of the current invention against the foaming characteristics of three commercially available shampoos.

Formulations

Four formulations were examined for their foaming performance. Three commercially available shampoos:

Premium grade everyday shampoo,

No brand basic everyday shampoo,

Medicated Anti-dandruff shampoo containing 2% ketoconazole,

The shampoo of the current invention based on Example 1.

Methodology

The method for measuring foaming is derived from the CIPAC Handbook, Chapter 7.

50 mL of the standard hard water at 342 ppm hardness is poured into a 100 mL standard stoppered cylinder. Into this 0.01 grams of shampoo is weighed. The cylinder is stoppered and inverted 30 times at a rotation of 180° C. and then placed on a flat surface and left undisturbed throughout the test period.

Since shampoos employ the use of highly foaming surfactants it was necessary to use an amount in these experiments that would be able to provide measurable foam volumes as well as show any potential differences between the shampoos. While 0.01 grams of shampoo may be a small amount it was able to provide a satisfactory foam that was measurable.

Results

The foam volume was measured at three temperatures: 23° C., 35° C. and 40° C. at initial, 30 second, 1 minute, 2 minutes, 3 minutes and 5 minutes. The measuring cylinders containing the shampoo solutions were kept at the specified temperatures for the duration of the test.

A=Premium Everyday Shampoo

B=Basic Everyday Shampoo

C=Medicated Shampoo with 2% ketoconazole

D=Shampoo of the current invention (Example 1)

TABLE 1

Foam Volum at 23° C.

| | Foam Volume (mL) | | | |
|---|---|---|---|---|
| Time | A | B | C | D |
| Initial | 55 | 60 | 40 | 44 |
| 30 seconds | 46 | 48 | 35 | 44 |
| 1 minute | 46 | 46 | 35 | 43 |
| 2 minutes | 44 | 46 | 35 | 42 |
| 3 minutes | 44 | 45 | 34 | 42 |
| 5 minutes | 44 | 45 | 33 | 42 |

TABLE 2

Foam Volume at 35° C.

| | Foam Volume mL | | | |
|---|---|---|---|---|
| Time | A | B | C | D |
| Initial | 45 | 45 | 49 | 53 |
| 30 seconds | 35 | 38 | 40 | 44 |
| 1 minute | 35 | 38 | 40 | 44 |
| 2 minutes | 35 | 38 | 38 | 44 |
| 3 minutes | 35 | 38 | 38 | 44 |
| 5 minutes | 35 | 38 | 38 | 44 |

TABLE 3

Foam Volume at 40° C.

| Time | Foam Volume (mL) | | | |
|---|---|---|---|---|
| | A | B | C | D |
| Initial | 55 | 55 | 55 | 50 |
| 30 seconds | 45 | 47 | 45 | 40 |
| 1 minute | 45 | 45 | 43 | 40 |
| 2 minutes | 44 | 45 | 43 | 40 |
| 3 minutes | 44 | 45 | 43 | 40 |
| 5 minutes | 44 | 45 | 43 | 40 |

Reproducibility between the results was also checked. Using the premium everyday shampoo the above experimentation was repeated a further three times with the standard water at 23° C. Below are the results:

TABLE 4

Reproducibility in measured foam volume for the premium everyday shampoo.

| Time | Foam Volume (mL) | | |
|---|---|---|---|
| | 1 | 2 | 3 |
| Initial | 45 | 47 | 50 |
| 30 seconds | 37 | 39 | 43 |
| 1 minute | 37 | 38 | 42 |
| 2 minutes | 37 | 38 | 42 |
| 3 minutes | 36 | 38 | 41 |
| 5 minutes | 35 | 38 | 41 |

When these results are compared to the results obtained earlier (table 1 shampoo A) there is a consistent variation of approximately ±5 mL.

The measured foam volume for the four shampoos tested demonstrate that the shampoo of the current invention performs as well as commercially available products at foam generation an maintenance. This is also true when the water temperature was increased from cool temperatures to temperatures that imitate shower temperature.

Aesthetic Acceptability

To assess the commercial utility and the aesthetic acceptability of the non-aqueous clotrimazole shampoo, a blind study was carried out in which 5 volunteers were provided with 4 shampoo products labelled A, B, C and D. After using each shampoo the volunteers were required to fill out a simple questionnaire concerning the performance of each shampoo.

Experimentation:

The four shampoos used in the blind study were:

Shampoo A: Non-aqueous Clotrimazole Shampoo according to example 1.

Shampoo B: Premium Grade Everyday Shampoo

Shampoo C: Medicated Anti-dandruff Shampoo containing 2% Ketoconazole

Shampoo D: Basic Standard Everyday Grade Shampoo

The volunteers were provided with 60 grams of each shampoo in a 100 mL HDPE pump pack. Along with the shampoo they were provided with a questionnaire to fill out when they had finished evaluating the shampoo.

Over a period of a fortnight the volunteers tested the shampoos and filled out the questionnaire.

Results and Discussion:

The volunteers were asked to evaluated the following characteristics when using the shampoos:

Whether the shampoo lathered well.

How well the shampoo cleaned their hair.

The physical condition of the hair after using the shampoo.

Was the hair's manageability altered after using the shampoo.

Was there any eye/skin discomfort.

The results were collected and are represented in Tables 1–5.

Shampoos A, B and D performed well to moderately well in their ability to lather. In fact they lathered better than Shampoo C which is a 2% ketoconazole shampoo that is currently marketed to treat dandruff. All the shampoos rated highly in their ability to clean.

When the volunteers were asked to assess the hair condition after shampoo use, they responded that both Shampoo A and C showed no noticeable effect or some improvement. Shampoos B and D were thought to either have no noticeable effect or cause the hair to become brittle/dry.

In the category of Hair Manageability the majority of the volunteers felt that the Shampoo C was the best. It either had no affect or there was some improvement. Shampoos B and D either had no effect or worsened hair manageability after use. Shampoo A rated somewhere in between Shampoos C and B and D.

Sometimes when a shampoo is being used, the user experiences some adverse reaction to a component of the shampoo. Table 5 shows that all the shampoos performed well and that no shampoo is distinguished.

CONCLUSION

Shampoo A, the non-aqueous shampoo, does provide a good lather and adequately cleans the hair. It does not cause adverse effects to the hair condition and manageability. When compared to commercially available shampoos (Shampoo B, C and D) it performs equally as well.

It will be appreciated that the scope of this invention is not limited by specific disclosures and examples of this specification but extends to formulations which would be understood by a skilled addressee as being equivalent in nature and effect to those compositions specifically described.

The invention claimed is:

1. A substantially non-aqueous liquid shampoo composition comprising at least one detergent, at least one azole antifungal agent, an organic bulking agent selected from the group consisting of polyethylene glycol of a molecular weight of 200–800 and propylene glycol, and shampoo excipients, said organic bulking agent being miscible with water and miscible with said at least one detergent wherein the water content is less than 20% by weight of said composition and wherein said bulking agent is present in an amount greater than 20% by weight of said composition.

2. A substantially non-aqueous liquid shampoo composition as claimed in claim 1 wherein said organic bulking agent is present in amounts greater than 50% by weight of said composition.

3. A substantially non-aqueous liquid shampoo composition as claimed in claim 1 wherein said organic bulking agent is selected so as not to affect foam formation of said composition.

4. A substantially non-aqueous liquid shampoo composition as claimed in claim 1 wherein the at least one azole antifungal agent, is selected from the group consisting of clotrimazole and ketoconozole.

5. A method of topically treating a dermal infection or condition comprising the step of applying a substantially non-aqueous liquid shampoo composition as claimed in claim 1 to the skin or hair of a patient in need of such treatment.

6. A method of topically treating a dermal infection or condition as claimed in claim 5 wherein the azole antifungal agent is selected from the group consisting of clotrimazole and ketoconazole.

7. A substantially non-aqueous liquid shampoo composition as claimed in claim 1, wherein said polyethylene glycol is PEG 400.

8. A substantially non-aqueous liquid shampoo composition as claimed in claim 1, wherein the water content is less than 15% by weight of said composition.

9. A substantially non-aqueous liquid shampoo composition as claimed in claim 1, wherein said at least one detergent is selected from the group consisting of an alkyl sulphate, an alkyl ether sulphate, and a sulphosuccinate.

10. A substantially non-aqueous liquid shampoo composition as claimed in claim 1, wherein the azole antifungal agent is an imidazole.

11. A substantially non-aqueous liquid shampoo composition as claimed in claim 1, further comprising a foam booster.

12. A method of topically treating a dermal infection or condition as claimed in claim 5, wherein said azole antifungal agent is an imidazole.

* * * * *